United States Patent
Thai et al.

(10) Patent No.: US 11,976,317 B2
(45) Date of Patent: May 7, 2024

(54) PRINTED TEST STRIPS TO DETERMINE GLUCOSE CONCENTRATION IN AQUEOUS LIQUIDS

(71) Applicant: SUN CHEMICAL CORPORATION, Parsippany, NJ (US)

(72) Inventors: Quang Minh Thai, Mühlheim am Main (DE); Michael Hirthammer, Mannheim (DE)

(73) Assignee: Sun Chemical Corporation, Parsippany, NJ (US)

( * ) Notice: Subject to any disclaimer, the term of this patent is extended or adjusted under 35 U.S.C. 154(b) by 418 days.

(21) Appl. No.: 16/604,633

(22) PCT Filed: Apr. 16, 2018

(86) PCT No.: PCT/US2018/027752
§ 371 (c)(1),
(2) Date: Oct. 11, 2019

(87) PCT Pub. No.: WO2018/194964
PCT Pub. Date: Oct. 25, 2018

(65) Prior Publication Data
US 2021/0115495 A1    Apr. 22, 2021

Related U.S. Application Data

(60) Provisional application No. 62/486,485, filed on Apr. 18, 2017.

(51) Int. Cl.
*C12Q 1/54* (2006.01)

(52) U.S. Cl.
CPC ..................................... *C12Q 1/54* (2013.01)

(58) Field of Classification Search
CPC ... C12Q 1/54; C12Q 1/28; C12Q 1/26; C12Q 1/58; C12Q 1/60; C12Q 1/689;
(Continued)

(56) References Cited

U.S. PATENT DOCUMENTS 2,981,606 A     4/1961 Keston
3,104,209 A *   9/1963 Scott .................. C12Q 1/54
                                                    436/95

(Continued)

FOREIGN PATENT DOCUMENTS

CA      1 185 153      4/1985
CA      2019424        6/1990

(Continued)

OTHER PUBLICATIONS

Methyl Cellulose, Feb. 28, 2014, Sigma Aldrich, pp. 1-2 p. 1, Para [3].

(Continued)

*Primary Examiner* — Adam Weidner
*Assistant Examiner* — Trent R Clarke
(74) *Attorney, Agent, or Firm* — Marian E. Fundytus; Ostrolenk Faber LLP.

(57) ABSTRACT

The present invention provides devices, and a method for preparing the devices, for measuring glucose concentration in a liquid sample. The devices are typically in the form of test strips. The test strips are printed with a reagent varnish comprising glucose oxidase, peroxidase, chromogen, and neutralizer. The chromogen in the reagent varnish changes color when the reagent varnish is exposed to glucose.

19 Claims, 3 Drawing Sheets

(58) Field of Classification Search
CPC .......... C12Q 2326/00; C12Q 2600/118; C12Q 2600/16; C12Q 1/04; C12Q 1/24; B01L 2300/0825; B01L 3/5023; B01L 2200/147; B01L 2200/16; B01L 2300/021; B01L 2300/0887; B01L 2400/0406; C09F 1/02; C12N 9/96; G01N 2800/18; G01N 2800/50; G01N 33/521; G01N 33/5302; G01N 33/54386; G01N 33/56955; G01N 33/6893; G01N 33/726; G01N 33/98; G01N 21/78; G01N 21/8483; G01N 2469/10; G01N 33/525; G01N 33/526; G01N 33/535; G01N 33/5438; G01N 33/558; G01N 33/5762; G01N 33/5764; Y10S 435/805; Y10S 435/81; Y10S 435/849; Y10S 436/808; Y10S 436/81; Y10S 436/817; Y10S 436/901; Y10S 530/866; A61B 5/14514; A61B 5/14532; Y10T 436/144444; Y10T 436/146666; Y10T 436/173076
See application file for complete search history.

(56) References Cited

U.S. PATENT DOCUMENTS

| | | | |
|---|---|---|---|
| 3,290,228 A | 12/1966 | Clissold et al. | |
| 3,802,842 A | 4/1974 | Ritterscorf et al. | |
| 3,964,871 A | 6/1976 | Hochstrasser | |
| 4,288,541 A * | 9/1981 | Magers | C12Q 1/54 436/95 |
| 4,318,984 A * | 3/1982 | Magers | C12Q 1/28 435/14 |
| 4,340,669 A | 7/1982 | Bauer | |
| 4,427,770 A | 1/1984 | Chen et al. | |
| 4,604,264 A | 8/1986 | Rothe et al. | |
| 4,786,595 A * | 11/1988 | Arai | C12Q 1/26 422/421 |
| 5,093,082 A * | 3/1992 | Watanabe | C12Q 1/54 422/424 |
| 5,124,128 A | 6/1992 | Hildenbrand et al. | |
| 5,183,742 A | 2/1993 | Omoto et al. | |
| 5,378,638 A | 1/1995 | Deeg et al. | |
| 6,531,322 B1 | 3/2003 | Jurik et al. | |
| 2008/0145940 A1 | 6/2008 | Menon | |

FOREIGN PATENT DOCUMENTS

| | | |
|---|---|---|
| DE | 198 45 771 A1 | 3/2000 |
| WO | WO 02/103353 A2 | 12/2002 |

OTHER PUBLICATIONS

International Search Report issued in International Application No. PCT/US18/27752, dated Jul. 11, 2018.
Written Opinion of the International Searching Authority issued in International Application No. PCT/US18/27752, dated Jul. 11, 2018.
International Preliminary Report on Patentability issued in Application No. PCT/US18/27752, dated Jun. 22, 2019.
Cha and He, Development of cellulose paper testing strips for quick measurement of glucose using chromogen agent. Carbohydrate Polymers, May 2012 (DOI: 10.1016/j.carbpol.2012.02.028).
Wilson, et al., A low cost inkjet-printed glucose test strip system for resource-poor settings. Journal of Diabetes Science and Technology, vol. 9(6):1275-1281, 2015.

* cited by examiner

PRINTED TEST STRIPS TO DETERMINE GLUCOSE CONCENTRATION IN AQUEOUS LIQUIDS

CROSS REFERENCE TO RELATED APPLICATIONS

This application claims priority to U.S. Provisional Application No. 62/486,485, filed 18 Apr. 2017, which is hereby incorporated herein in its entirety.

FIELD OF THE INVENTION

The present invention is related to devices for testing the concentration of glucose in liquid samples. The devices of the present invention are in the form of test strips printed with a reagent varnish. The test strips of the present invention are suitable to test glucose concentration in biological fluids, such as urine.

BACKGROUND OF THE INVENTION

Testing for glucose concentration in biological fluids, such as blood and urine, can aid in the diagnosis or monitoring of diseases, such as diabetes. One way to test the concentration of glucose in a liquid is to dip a test strip comprising reagents that react in the presence of glucose into the liquid to be tested. Most of the commercially available glucose test strips are prepared by impregnation of reagent solutions into absorbent substrates, such as filter paper. Others are extruded or blade coated with a complex structure. There remains a need for a more efficient, cost-effective method of producing glucose test strips.

U.S. Pat. No. 3,964,871 describes a device for testing glucose concentration in biological fluids which comprises a support-member impregnated with indicator reagent solutions. The preferred support-member is an absorbent material, which is then affixed to a hydrophobic second support member, such as a polymer film. A plurality of reagent impregnated absorbent support-members, each impregnated with a different reagent solution, are affixed to the second support member in discrete zones.

U.S. Pat. No. 4,340,669 provides a method to detect and differentiate between very high concentrations of glucose in biological fluids. The primary chromogen used in the reagent solutions is m-anisidine, which is toxic. Secondary chromogens are used to enable differentiating at very high concentrations of glucose, such as between 2,000 mg/dL and 5,000 mg/dL.

U.S. Pat. No. 4,427,770 discloses an analytical element produced by impregnating a carrier with a solution of 4-aminoantipyrine and a benzoic acid, a glucose oxidase, and peroxidase. A second solution of a semi-permeable polymer is then applied to the carrier.

EP 0078 971 (CA 1185153) describes a vehicle for glucose determination containing glucose oxidase, peroxidase, a chromogen, a nitrate, and, where appropriate, a UV-absorber. These agents are applied to the support matrix via impregnation.

DE 3809523 (U.S. Pat. No. 5,124,128) describes a process for the production of porous membranes, the membranes produced therewith, and their use as support matrices in test strips. The support with the membrane is immersed in the reagent solution. Under production conditions, impregnation can be done by means of an extrusion caster.

DE 4024544 (U.S. Pat. No. 5,378,638) describes a support layer containing a reagent applied in a defined pattern by means of an inkjet process. The pattern comprises several sets of compartments, with each set containing a different reagent. One set of compartments contains a reagent that is bound to the support layer. One or more other sets of compartments contain reagents that are soluble in the fluid to be tested, i.e. they are elutable. Upon application of the test fluid, the elutable reagents are dissolved in the test fluid, and carried to the bound reagent, whereby a reaction takes place if glucose is present.

DE 1984 5771 describes glucose test strips which contain a reactive composition of 4-6 wt % peroxidase, 2-3 wt % glucose oxidase, 18-19 wt % o-tolidine, 4-6 wt % polycarbon acid, and 66-72 wt % polypeptide binder.

DE 6021 9472 (WO 02/103353) describes a dry chemical test system for detecting glucose in animal urine, particularly cats. The chemical test system comprises two indicators, 4-AAP/phenol and potassium iodide for the detection and quantification of different concentrations of glucose in urine. In addition, the chemical test system contains an inhibitor that reacts with the oxidized indicator until the inhibitor is saturated, thus providing a minimum threshold at which the presence of glucose will be indicated.

EP 0113896 (U.S. Pat. No. 4,604,264) describes test strips wherein the reagents are coated on a polymer fabric with a slotted nozzle or a rake. Between the reagent layer and the gripping film there is an additional absorbent layer. The various components are preferably held together by a transparent cover net.

DE 3922495 (CA 2019424) describes a multilayer system, wherein the chromogen is integrated in a polymer casting solution. This polymer solution and the GOD/POD/binder matrix are applied in separate layers to a perforated polyester fabric by the use of a blade. A double adhesive tape is used to stick the coated polyester film on a support polymer film, wherein a polymer net covers the upper side of the complex.

U.S. Pat. No. 5,183,742 describes a test device for detecting various substances, such as glucose, protein urobilinogen, and/or occult blood, in body fluids. The reagent solutions are solvent-based, wherein the reagents and other ingredients are dissolved in organic solvents. The reagent solutions can be applied to a substrate, such as a polystyrene film, by several methods, preferably silk-screen printing.

Cha and He (Development of cellulose paper testing strips for quick measurement of glucose using chromogen agent. Carbohydrate Polymers, May 2012 (DOI: 10.1016/j.carbpol.2012.02.028)), describe cellulose paper based glucose test strips comprising 2,4,6-tribromo-3-hydroxy benzoic acid (TBHBA) as the chromogen, glucose oxidase and peroxidase as the enzyme catalysts, and gelation as the enzyme stabilizer. The reagents are applied to the substrate by soaking the substrate in the reagent solution.

Wilson, et al. (A low cost inkjet-printed glucose test strip system for resource-poor settings. *Journal of Diabetes Science and Technology*, Vol. 9(6):1275-1281, 2015) describe a low cost inkjet printed glucose test strip system. Three of the ink cartridges in an inkjet printer are replaced with cartridges containing three different reagent solutions: a glucose oxidase solution, a peroxidase solution, and a chromogen solution. The reagent solutions are each printed in separate layers.

SUMMARY OF THE INVENTION

The present invention provides simple devices for the determination of glucose in biological fluids. In a preferred embodiment, the devices are in the form of test strips upon which a formulation containing reagents for the detection of glucose are printed.

In a particular aspect, the present invention provides a method of preparing an indicator test strip for determining glucose concentration in a liquid sample, comprising:
a) providing a reagent varnish, wherein the reagent varnish comprises:
  i. one or more binders;
  ii. one or more oxidase enzymes;
  iii. one or more peroxidase enzymes;
  iv. one or more chromogens;
  v. one or more neutralizers; and
  vi. water;
b) providing a substrate;
c) printing the reagent varnish onto the substrate; and
d) drying the reagent varnish on the substrate;
wherein the test strip changes color upon exposure to glucose.

In certain embodiments, the reagent varnish is printed on the substrate via flexographic printing, gravure printing, or screen printing.

In particular embodiments, multiple discrete regions of the substrate are printed at different coating weights, to provide varying amounts of reagent varnish in each region, wherein the discrete regions provide differing intensities of color change upon exposure to glucose.

In one embodiment, the liquid sample is urine.

BRIEF DESCRIPTION OF THE DRAWINGS

FIG. 1: FIG. 1(a) depicts a gravure cylinder 1, with a unique pattern of engraved bands 2 across the print direction. FIG. 1(b) depicts a gravure cylinder 1, with a unique pattern of engraved bands 3 parallel to the print direction.

FIG. 2: FIG. 2(a) depicts a gravure cylinder 1, with a unique pattern of engraved bands 4, 5, and 6, having different cell depths and aligned across the print direction. FIG. 2(b) depicts a gravure cylinder 1, with a unique pattern of engraved bands 7, 8, and 9, having different cell depths and aligned parallel to the print direction.

FIG. 3.

FIG. 4.

DETAILED DESCRIPTION OF THE INVENTION

The present invention provides simple devices for the determination of glucose in biological fluids. The devices are both simple to use, and can be produced with maximum efficiency. The devices are provided in the form of test strips. The test strips of the present invention are particularly suited to measuring glucose concentration in a urine sample.

The test strips are prepared by printing a reagent varnish on a substrate. The reagent varnish is preferably applied by either flexographic, gravure, or silk-screen printing.

The reagent varnish comprises one or more binders, one or more oxidases, one or more peroxidases, one or more chromogens, one or more neutralizers, and water.

Definitions

In this application, the use of the singular includes the plural unless specifically stated otherwise. As used herein, the singular forms "a," "an" and "the" are intended to include the plural forms as well, unless the context clearly indicates otherwise.

In this application, the use of "or" means "and/or" unless stated otherwise.

As used herein, the terms "comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

As used herein, ranges and amounts can be expressed as "about" a particular value or range. "About" is intended to also include the exact amount. Hence "about 5 percent" means "about 5 percent" and also "5 percent." "About" means within typical experimental error for the application or purpose intended.

As used herein, the term "reagent varnish" refers to the prepared solution of binder, enzymes, chromogens, and other suitable ingredients. The amount of enzymes in the reagent varnish solution is expressed as "U/dl," wherein "U" means International Units (IU).

As used herein, the term "chromogen" refers to a substance that can be converted to a dye or other colored compound when oxidized. In the present invention, the chromogens typically react with hydrogen peroxide, in a reaction catalyzed by a peroxidase, to form an oxidized colored compound.

Glucose Test Devices

The present invention provides simple devices for the determination of glucose in biological fluids. In a preferred embodiment, the present invention relates to the determination of glucose in urine, by applying a glucose-oxidase/peroxidase enzyme system (GOD/POD). The GOD/POD and other ingredients are dissolved in a binder solution, to prepare a reagent varnish. The reagent varnish contains one or more chromogens that will change color when glucose is present in the fluid sample. The reagent varnish is printed on a substrate. Methods of printing include, but are not limited to, flexographic, gravure, and screen printing.

The present invention provides a method to produce the test strips, and the test strips resulting from the method.

While most of the commercially available glucose test strips are made by impregnation of a reagent solution into the substrate, others are blade coated or extruded with a complex structure. The present invention comprises printing the ingredient mixture (i.e. reagent varnish) on a simple paper, paperboard, or plastic film substrate, for easy production of test strips.

The method of the present invention is based on a bienzyme system, coupled with one or more chromogens, to detect glucose in a fluid sample. The enzymes are one or more oxidases, preferably glucose oxidases, and one or more peroxidases. The glucose oxidase catalyzes the conversion of glucose to gluconate and hydrogen peroxide. The peroxidase then catalyzes the reaction between the hydrogen peroxide and the chromogen, producing a color change.

In a particular aspect, the present invention provides a method of preparing an indicator test strip for determining glucose concentration in a liquid sample, comprising:
a) providing a reagent varnish, wherein the reagent varnish comprises:
  i. one or more binders;
  ii. one or more oxidase enzymes;
  iii. one or more peroxidase enzymes;
  iv. one or more chromogens;
  v. one or more neutralizers; and
  vi. water;
b) providing a substrate;
c) printing the reagent varnish onto the substrate; and
d) drying the reagent varnish on the substrate;
wherein the test strip changes color upon exposure to glucose.

The oxidase is preferably glucose oxidase. Glucose oxidase catalyzes the reaction between glucose, oxygen and water to produce gluconate and hydrogen peroxide. The glucose oxidase is typically present in an amount of about 10,000 U/dl to about 50,000 U/dl. For example the glucose may be present in an amount of about 10,000 U/dl to 45,000 U/dl; or about 10,000 U/dl to about 40,000 U/dl; or about 10,000 U/dl to about 35,000 U/dl; or about 10,000 U/dl to about 30,000 U/dl; or about 10,000 U/dl to about 25,000 U/dl; or about 10,000 U/dl to about 20,000 U/dl; or about 10,000 U/dl to about 15,000 U/dl; or about 15,000 U/dl to about 50,000 U/dl; 15,000 U/dl to about 45,000 U/dl; or about 15,000 U/dl to about 40,000 U/dl; or about 15,000 U/dl to about 35,000 U/dl; or about 15,000 U/dl to about 30,000 U/dl; or about 15,000 U/dl to about 25,000 U/dl; or about 15,000 U/dl to about 20,000 U/dl; or about 20,000 U/dl to about 50,000 U/dl; or about 20,000 U/dl to about 45,000 U/dl; or about 20,000 U/dl to about 40,000 U/dl; or about 20,000 U/dl to about 35,000 U/dl; or about 20,000 U/dl to about 30,000 U/dl; or about 20,000 U/dl to about 25,000 U/dl; or about 25,000 U/dl to about 50,000 U/dl; or about 25,000 U/dl to about 45,000 U/dl; or about 25,000 U/dl to about 40,000 U/dl; or about 25,000 U/dl to about 35,000 U/dl; or about 25,000 U/dl to about 30,000 U/dl; or about 30,000 U/dl to about 50,000 U/dl; or about 30,000 U/dl to about 45,000 U/dl; or about 30,000 U/dl to about 40,000 U/dl; or about 30,000 U/dl to about 35,000 U/dl; or about 35,000 U/dl to about 50,000 U/dl; or about 35,000 U/dl to about 45,000 U/dl; or about 35,000 U/dl to about 40,000 U/dl; or about 40,000 U/dl to about 50,000 U/dl; or about 40,000 U/dl to about 45,000 U/dl; or about 45,000 U/dl to about 50,000 U/dl.

Suitable glucose oxidases include those derived from fungi and insects, including glucose oxidase, glucose-1-oxidase, and glucose-2-oxidase. Typically, glucose oxidase derived from fungi is used in various industries, including biological tests. Suitable fungal sources of glucose oxidase include, but are not limited to, *Penicillium notatum, Aspergillus niger, Penicillium amagasakiense, Penicillium purpurogenum* No. 778, *Phanerochaete chrysosporium, Aspergillus flavus, Pencillium* sp, *Fusarium* sp, *Aspergillus terreus*, and the like.

The present invention comprises one or more peroxidases. Peroxidase catalyzes the reaction of the hydrogen peroxide produced by the reaction catalyzed by glucose oxidase, with the one or more chromogens to produce a color change in the reagent varnish. The peroxidase is typically present in an amount of about 10,000 U/dl to about 45,000 U/dl. For example, the peroxidase may be present in an amount of about 10,000 U/dl to about 40,000 U/dl; or about 10,000 U/dl to about 35,000 U/dl; or about 10,000 U/dl to about 30,000 U/dl; or about 10,000 U/dl to about 25,000 U/dl; or about 10,000 U/dl to about 20,000 U/dl; or about 10,000 U/dl to about 15,000 U/dl; or about 15,000 U/dl to about 45,000 U/dl; or about 15,000 U/dl to about 40,000 U/dl; or about 15,000 U/dl to about 35,000 U/dl; or about 15,000 U/dl to about 30,000 U/dl; or about 15,000 U/dl to about 25,000 U/dl; or about 15,000 U/dl to about 20,000 U/dl; or about 20,000 U/dl to about 45,000 U/dl; or about 20,000 U/dl to about 40,000 U/dl; or about 20,000 U/dl to about 35,000 U/dl; or about 20,000 U/dl to about 30,000 U/dl; or about 20,000 U/dl to about 25,000 U/dl; or about 25,000 U/dl to about 45,000 U/dl; or about 25,000 U/dl to about 40,000 U/dl; or about 25,000 U/dl to about 35,000 U/dl; or about 25,000 U/dl to about 30,000 U/dl; or about 30,000 U/dl to about 45,000 U/dl; or about 30,000 U/dl to about 40,000 U/dl; or about 30,000 U/dl to about 35,000 U/dl; or about 35,000 U/dl to about 45,000 U/dl; or about 35,000 U/dl to about 40,000 U/dl; or about 40,000 U/dl to about 45,000 U/dl.

Suitable peroxidases include those derived from plants, fungi, and bacteria. Suitable plant peroxidases include, but are not limited to, horseradish peroxidase, soybean peroxidase, turnip peroxidase, radish peroxidase, cabbage peroxidase, broccoli peroxidase, apple peroxidase, orange peroxidase, tobacco peroxidase, green pea peroxidase, pumpkin peroxidase, *papaya* peroxidase, banana peroxidase, combinations thereof, and the like. For example, horseradish peroxidase is typically used in a bienzyme test system for glucose. Suitable microbial sources of peroxidase (e.g. bacteria, cyanobacteria, fungi, actinomycetes, etc.) include those isolated from, but not restricted to, *Streptomyces thermoviolaceus, Bacillus subtilis, Pseudomonas* sp, *Citrobacter* sp, *Anabaena* sp, *Candida krusei, Coprinopsis cinerea, Phanerochaete chrysosporium, Streptomyces* sp, *Thermobifida fusca*, yeast, and the like.

The present invention comprises one or more chromogens. The chromogen reacts with the hydrogen peroxide, in a reaction catalyzed by the peroxidase, to form an oxidized chromogen, to effect a color change when the reagent varnish is exposed to glucose in the fluid sample. One or more chromogens may be used, and each chromogen is typically present in an amount of about 200 mg/dl to about 750 mg/dl. If more than one chromogen is used, the total amount of chromogens will be the sum of the amounts of each. For example, if two chromogens are used, the total amount of chromogens can be about 400 mg/dl to about 15,000 mg/dl. In certain embodiments, each chromogen may be present in an amount of about 200 mg/dl to about 700 mg/dl; or about 200 mg/dl to about 650 mg/dl; or about 200 mg/dl to about 600 mg/dl; or about 200 mg/dl to about 550 mg/dl; or about 200 mg/dl to about 500 mg/dl; or about 200 mg/dl to about 450 mg/dl; or about 200 mg/dl to about 400 mg/dl; or about 200 mg/dl to about 350 mg/dl; or about 200 mg/dl to about 300 mg/dl; or about 200 mg/dl to about 250 mg/dl; or about 250 mg/dl to about 750 mg/dl; or about 250 mg/dl to about 700 mg/dl; or about 250 mg/dl to about 650 mg/dl; or about 250 mg/dl to about 600 mg/dl; or about 250 mg/dl to about 550 mg/dl; or about 250 mg/dl to about 500 mg/dl; or about 250 mg/dl to about 450 mg/dl; or about 250 mg/dl to about 400 mg/dl; or about 250 mg/dl to about 350 mg/dl; or about 250 mg/dl to about 300 mg/dl; or about 300 mg/dl to about 750 mg/dl; or about 300 mg/dl to about 700 mg/dl; or about 300 mg/dl to about 650 mg/dl; or about 300 mg/dl to about 600 mg/dl; or about 300 mg/dl to about 550 mg/dl; or about 300 mg/dl to about 500 mg/dl; or about 300 mg/dl to about 450 mg/dl; or about 300 mg/dl to about 400 mg/dl; or about 300 mg/dl to about 350 mg/dl; or about 350 mg/dl to about 750 mg/dl; or about 350 mg/dl to about 700 mg/dl; or about 350 mg/dl to about 650 mg/dl; or about 350 mg/dl to about 600 mg/dl; or about 350 mg/dl to about 550 mg/dl; or about 350 mg/dl to about 500 mg/dl; or about 350 mg/dl to about 450 mg/dl; or about 350 mg/dl to about 400 mg/dl; or about 400 mg/dl to about 750 mg/dl; or about 400 mg/dl to about 700 mg/dl; or about 400 mg/dl to about 650 mg/dl; or about 400 mg/dl to about 600 mg/dl; or about 400 mg/dl to about 550 mg/dl; or about 400 mg/dl to about 500 mg/dl; or about 400 mg/dl to about 450 mg/dl; or about 450 mg/dl to about 750 mg/dl; or about 450 mg/dl to about 700 mg/dl; or about 450 mg/dl to about 650 mg/dl; or about 450 mg/dl to about 600 mg/dl; or about 450 mg/dl to about 550 mg/dl; or about 450 mg/dl to about 500 mg/dl; or about 500 mg/dl to about 750 mg/dl; or about 500 mg/dl to about 700 mg/dl; or about 500 mg/dl to about 650 mg/dl; or about 500 mg/dl to about 600 mg/dl; or about 500 mg/dl to about 550 mg/dl; or about 550 mg/dl to about 750 mg/dl; or about 550 mg/dl to about 700 mg/dl; or about 550 mg/dl to about 650 mg/dl; or about 550 mg/dl to about 600 mg/dl; or about 600 mg/dl to about 750 mg/dl; or about 600 mg/dl to about 700 mg/dl; or about 600 mg/dl to about 650 mg/dl; or about 650 mg/dl to about 750 mg/dl; or about 650 mg/dl to about 700 mg/dl; or about 700 mg/dl to about 750 mg/dl.

Suitable chromogens include, but are not limited to: 4-aminoantipyrin (4-AAP); antipyrine; tri bromo hydroxybenzoic acid (TBHBA); o-tolidine; 4-hydroxybenzoic acid; phenol, 4-bromophenol; 4-chlorophenol; 3,3'5,5'-tetramethylbenzidin (TMB); 2,2'-azino-bis(3-ethylbenzothiasoline-6-sulphonic acid (ABTS); combinations thereof; and the like.

The reagent varnish of the present invention comprises one or more neutralizers. The neutralizers react with the oxidized form of the chromogen below a threshold level of glucose (e.g. 30 mg/dl), to bring the chromogen back to reduced form. Below the threshold level, the reagent varnish remains colorless. Once the threshold level of glucose is reached, and the neutralizer is saturated, the chromogen is present in oxidized form, and the reagent varnish changes color. The neutralizer is typically present in an amount of about 5 mg/dl to about 25 mg/dl. For example, the neutralizer may be present in an amount of about 5 mg/dl to about 20 mg/dl; or about 5 mg/dl to about 15 mg/dl; or about 5 mg/dl to about 10 mg/dl; or about 10 mg/dl to about 25 mg/dl; or about 10 mg/dl to about 20 mg/dl; or about 10 mg/dl to about 15 mg/dl; or about 15 mg/dl to about 25 mg/dl; or about 15 mg/dl to about 20 mg/dl; or about 20 mg/dl to about 25 mg/dl.

Suitable neutralizers include, but are not limited to, L-cysteine, mercaptans, thiosulfates, gallic acid, ascorbic acid, combinations thereof, and the like.

The enzymes, chromogens, and neutralizers are typically dissolved or dispersed in a binder solution or dispersion. The binder solution or dispersion typically has a solids content of 1 wt % to 3 wt %, based on the total weight of the binder solution or dispersion. The viscosity of the binder solution or dispersion is typically about 15 cps to about 400 cps.

Suitable binders include, but are not limited to, methylcellulose, hydroxyl ethyl cellulose, ethylcellulose, polyvinylpyrrolidone, polyurethane (typically as a dispersion), gelatin, combinations thereof, and the like.

As described, the present invention employs a bienzyme system for detection of glucose in a fluid sample. The glucose oxidase catalyzes the conversion of glucose to gluconate and hydrogen peroxide. The peroxidase then catalyzes the reaction between the hydrogen peroxide and the chromogen, producing a color change.

In one embodiment, the reagent varnish comprises the chromogens 2,4,6-TBHBA and 4-AAP, and the color change is from colorless to a rose/pink or red, depending on the glucose concentration in the test liquid.

In another embodiment, the reagent varnish comprises TMB as the chromogen, and the color change is from colorless to blue.

It would also be possible to incorporate small amounts of colorant into the reagent varnishes, but this is typically not done as it may interfere with the perceived color change of the reagent varnish.

The reagent varnish can be applied to the substrate by any suitable method. Preferred methods include gravure printing, flexographic printing, and screen printing. It is to be understood that other methods, such as, for example, ink jet printing, could be used in the method of the present invention.

In gravure printing, the cylinder is typically engraved as a pattern along the cylinder width, providing a wet coating weight of about 4 g/m$^2$ to 25 g/m$^2$. The cylinder typically has about 10 lines/cm to about 140 lines/cm, engraved with a stylus angle of about 80° to about 150°. A cylinder can contain several patterns of vertical or horizontal engraved bands, depending on the cylinder.

Figure 1:
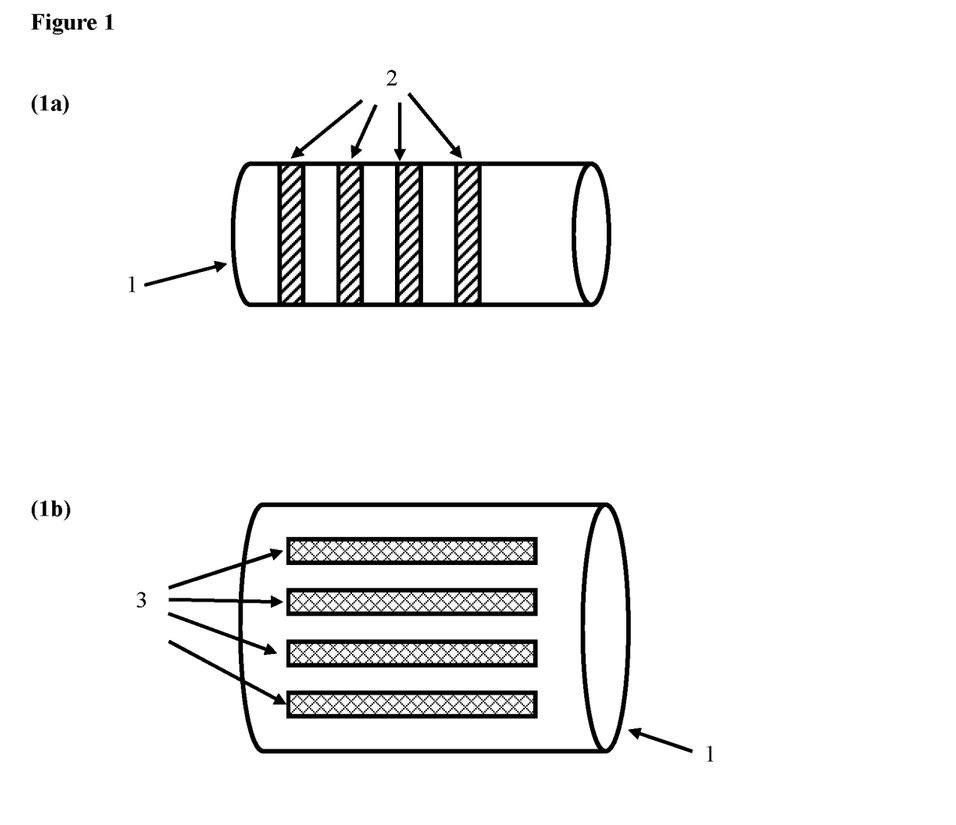
FIG. 1 shows engraved patterns on a gravure cylinder.
Figure 3:
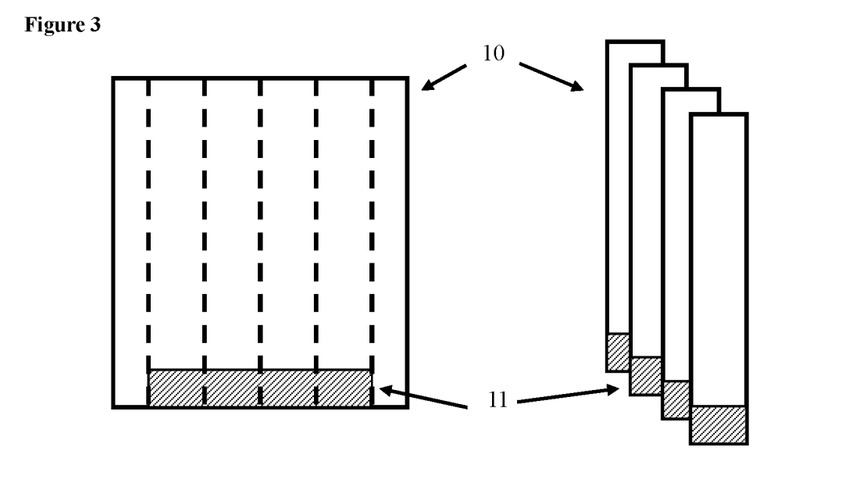
FIG. 3 shows test strips 10 printed with a single area printed with reagent varnish 11, before and after being cut into strips.

FIG. 1 shows different patterns of engraved bands of the same cell depth to print the same coating weight, with FIG. 1(a) showing a pattern of bands engraved across the print direction, and FIG. 1(b) showing a pattern of bands engraved parallel to the print direction. The corresponding test strips, having a single printed band of reagent varnish are shown in FIG. 3.

Figure 2:
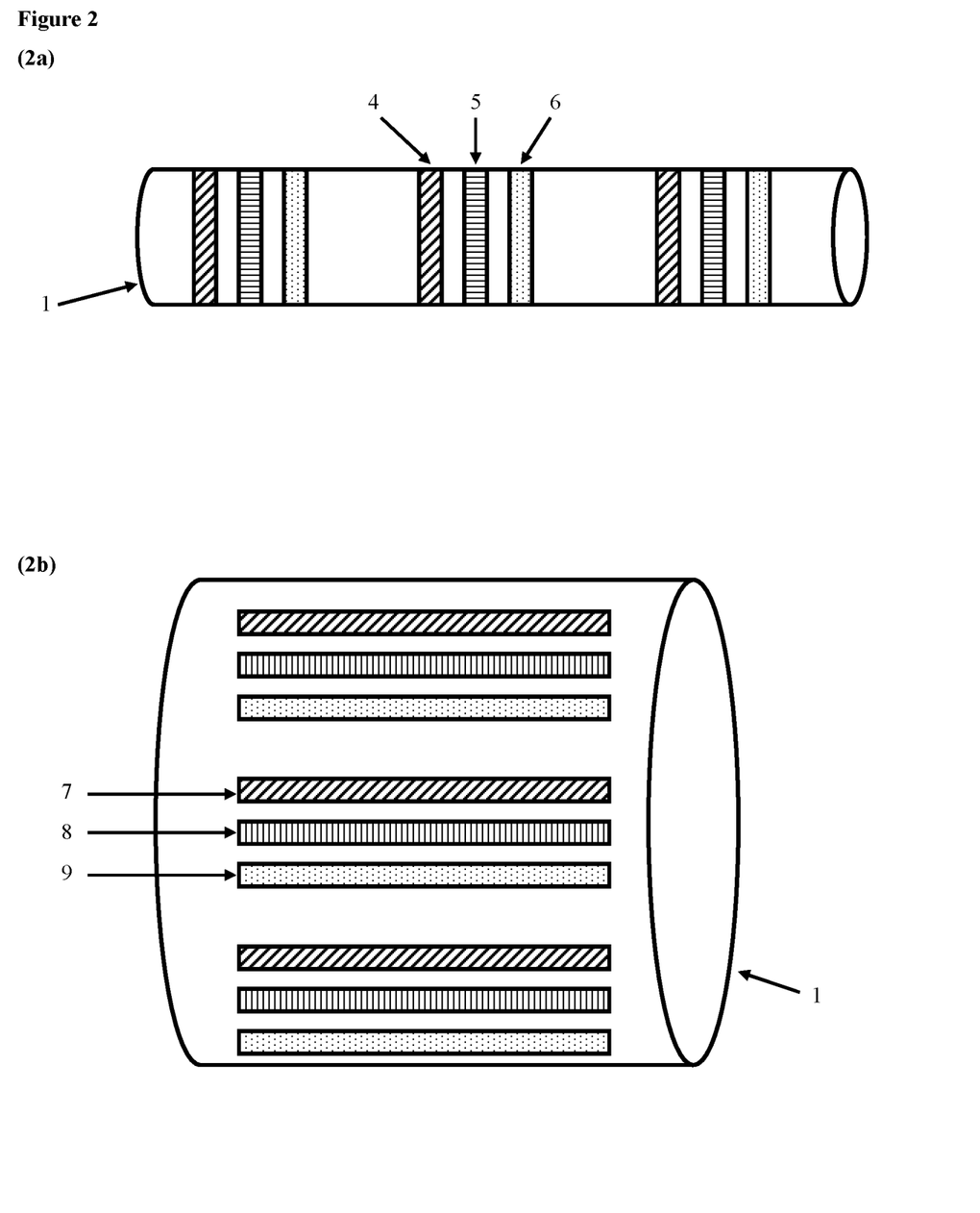
FIG. 2 shows patterns of different cell depths on a gravure cylinder.
Figure 4:
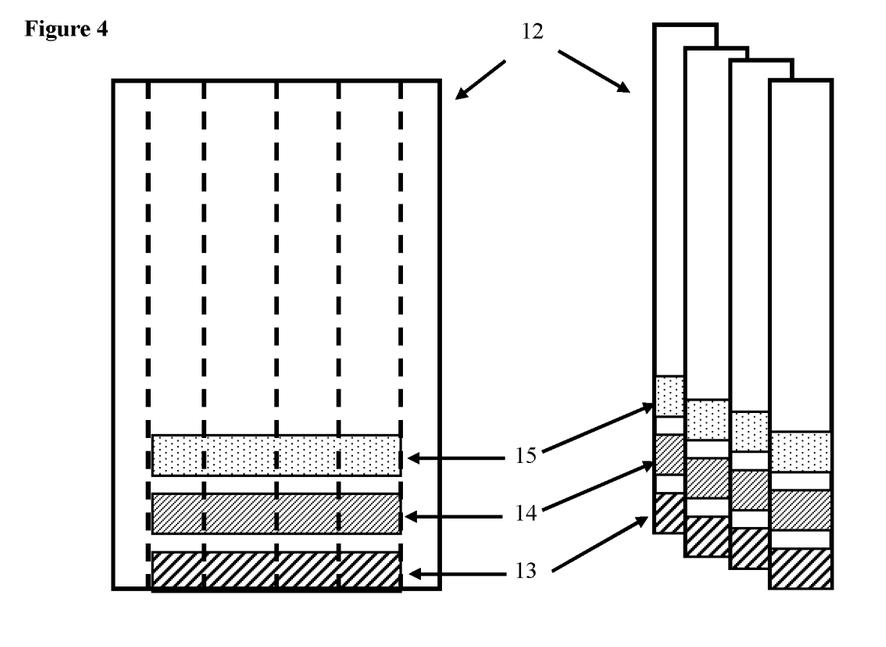
FIG. 4 shows test strips 12 printed with three discrete areas of printed reagent varnish (13, 14, and 15), each area being of a different coating weight, before and after being cut into strips.

FIG. 2 shows a pattern of a group of three repeating bands, with each of the bands being of a different cell depth, to print at different coating weights. Each of the three bands in the repeat set has a different amount of reagent varnish, and prints a different coating weight onto the substrate. This results in differing intensity of the color change in three levels, in order to achieve better control on determination of glucose content of the liquid sample. The corresponding test strips are shown in FIG. 4, having a group of three bands, each band having a different coating weight of reagent varnish.

Different cell depths on a gravure cylinder carry a different volume of reagent varnish. This results in application of different coating weights during printing. Table 1 describes the volume of reagent varnish in cells of different depths, and the corresponding coating weight of the printed reagent varnish, engraved at a stylus angle of 80°.

TABLE 1

Gravure cylinder different cell depths at stylus angle 80°
Gravure cylinder, stylus angle 80°

| Cell depth ($\mu m$) | Volume ($cm^3/m^2$) | Applied Weight (wet-$g/m^2$) |
|---|---|---|
| 35 | 13 | 4 |
| 45 | 16 | 5 |
| 80 | 27 | 8 |
| 110 | 37 | 11 |
| 200 | 80 | 24 |

Table 2 describes the volume of reagent varnish in cells of different depths, and engraved at different stylus angles.

TABLE 2

Gravure cylinder different cell depths at different stylus angles

| Cell depth ($\mu m$) | Stylus Angle 120° | Stylus angle 130° |
|---|---|---|
| | Volume $cm^3/m^2$ | |
| 33 | 11 | 10 |
| 45 | 15 | 13 |
| 60 | 22 | 18 |

In other embodiments, the reagent varnish is applied to the substrate by flexographic printing. In flexographic printing, the anilox roller is engraved, providing a wet coating weight of 2 $g/m^2$ to 10 $g/m^2$ on the substrate. Similar to the description for gravure printing, a flexographic printing plate can contain several patterns of vertical or horizontal bands (print areas). The print is cut into strips with defined width and length. A printing plate can also have a set of two or more different bands, which are full-tone or half-tone areas (30% to 100%). These areas have different amounts of the reagent varnish. Printing with the set of two or more bands results in differing intensity of the color change in order to achieve better control on determination of glucose content of the liquid sample. Table 3 describes a sample flexographic anilox roller with three bands of different tone/screen density (lines/cm).

TABLE 3

Sample flexographic roller with a set of three bands
Flexo Anilox roller

| Screen (L/cm) | Pick-up Volume ($cm^3/m^2$) | Applied Weight (wet $g/m^2$) |
|---|---|---|
| 100 | 11 | 4 |
| 80 | 15 | 6 |
| 55 | 21 | 8 |

In other embodiments, the reagent varnish can be applied to the substrate via screen printing. A blade is moved across the screen to fill the open mesh apertures with reagent varnish, a reverse stroke then causes the screen to touch the substrate along a line of contact. This causes the reagent varnish to wet the substrate and will be pulled out of the mesh apertures as the screen springs back after the blade has passed.

Typically, the substrate will be cellulose based, for example paper or paperboard substrates. In a preferred embodiment, the substrate will be a paper or paperboard substrate with a basic weight of equal to or greater than 80 $g/m^2$, such as, for example equal to or greater than 100 $g/m^2$. Preferably, the paper or paperboard will have a basic weight of equal to or greater than 150 $g/m^2$, and more preferably equal to or greater than 200 $g/m^2$. Heavier weight paper or paperboard provides dimensional stability under wet conditions. Although less common, it would also be possible to use other types of substrates, such as, for example, plastics, metals, or metal foils. Plastic films preferably have a thickness of equal to or greater than 40 $\mu m$ to provide a stable handle for the liquid test.

Especially preferred is coated paper used for graphic arts, preferably with a surface structure. The surface structure can be in the form of fine or bold linen surface, or irregular uneven surface. The surface structure prevents the reagent varnish from penetrating into the paper, while offering enough oxygen for the reaction. Preferably, the surface structure allows a good wetting of the test liquid (e.g. urine), and offers enough air space, which is required for an optimal reaction.

EXAMPLES

The following examples illustrate specific aspects of the present invention, and are not intended to limit the scope thereof in any respect, and should not be so construed.

Example 1. Gravure Reagent Varnish 1

A reagent varnish 1 for gravure printing was prepared according to the formula shown in Table 4.

TABLE 4

Formula of gravure reagent varnish 1

| Material | Weight |
|---|---|
| Methyl cellulose 400 cps | 1.3 gm |
| Glucose oxidase (GOD) | 20,000 U |
| Peroxidase (POD) | 16,500 U |
| 4-Aminoantipyrin (4-AAP) | 300 mg |
| 2,4,6 Tribromo-3-hydroxyl benzoic acid (TBHBA) | 300 mg |
| L-Cystein | 5 mg |
| Fill up with water to 100 gm | |

The Example 1 reagent varnish was printed on a gravure press, using a cylinder having engraved bands with a cell depth of about 70 $\mu m$. The substrate was MH 2384 EL from Mitsubishi, an embossed coated inkjet paper with linen surface. The basic weight of the substrate was 228 $g/m^2$, with a paper thickness of 295 $\mu m$. After printing, the prints were cut into strips (see FIG. 3) having a width of about 0.5 cm to about 1.0 cm, and a length of about 8 cm to about 10 cm. The strips were dipped into glucose-containing urine. After contact with glucose-containing urine, a visual color change from colorless to pink/rose-red occurred, where the color intensity indicated the level of glucose.

Example 2. Gravure Reagent Varnish 2

A reagent varnish 2 for gravure printing was prepared according to the formula shown in Table 5.

TABLE 5

Formula of gravure reagent varnish 2

| Material | Weight |
|---|---|
| Methyl cellulose 400 cps | 1.3 gm |
| Glucose oxidase (GOD) | 40,000 U |
| Peroxidase (POD) | 34,5000 U |
| 4-Aminoantipyrin (4-AAP) | 400 mg |
| 2,4,6 Tribromo-3-hydroxyl benzoic acid (TBHBA) | 400 mg |
| L-Cystein | 10 mg |
| Fill up with water to 100 gm | |

The Example 2 reagent varnish was printed on a gravure press, having a cylinder engraved with a set of three bands of different cell depths. The cell depths were 75 μm (Field 4), 50 μm (Field 5), and 30 μm (Field 6). As cell depth increases, the coating weight of reagent varnish applied to the substrate increases. The substrate was MH 2384 BL from Mitsubishi, an embossed inkjet paper with bold linen surface, having a basic weight of 228 g/m², and a paper thickness of 295 μm. After printing, the prints were cut into strips (see FIG. 4) having a width of about 0.5 cm to about 1.0 cm, and a length of about 8 cm to about 10 cm, for the glucose test. The color changes for each field at varying concentrations of glucose are shown in Table 6.

TABLE 6

Color change based on reagent varnish coating thickness on the substrate

| | COLOUR CHANGE colorless → pink/red | | |
|---|---|---|---|
| Glucose | 30 mg/dl | 50 mg/dl | >50 mg/dl |
| Field 4 | Slight | Moderate | Strong |
| Field 5 | Slight | Moderate | Moderate |
| Field 6 | None | None-very slight | Very slight |

The results in Table 6 show that, as the coating thickness increases, the sensitivity of the reagent varnish increases, so that the amount of color change can indicate varying concentrations of glucose in the liquid sample.

Example 3. Flexographic Reagent Varnish 3

A reagent varnish 3 for flexographic printing was prepared according to the formula shown in Table 7. Because it is for flexographic printing, Example 3 varnish preferably has a higher viscosity than Examples 1 and 2.

TABLE 7

Flexographic reagent varnish 3

| Material | Weight |
|---|---|
| Methyl cellulose 15 cps | 5.5 gm |
| Glucose oxidase (GOD) | 40,000 U |
| Peroxidase (POD) | 34,5000 U |
| 4-Aminoantipyrin (4-AAP) | 400 mg |
| 2,4,6 Tribromo-3-hydroxyl benzoic acid (TBHBA) | 400 mg |
| L-Cystein | 10 mg |
| Fill up with water to 100 gm | |

The Example 3 varnish was printed on a flexographic press, using a flexo plate and anilox roller that provided a pick-up volume of 20 cm³/m² to 30 cm³/m². The substrate was MH2384EL paper. The bands on the flexo plate were full-tone areas. After printing, the prints were cut into strips having a width of 0.5 cm to 1.0 cm, and a length of 8 cm to 10 cm, for the glucose test.

Example 4. Flexographic Reagent Varnish 4

A reagent varnish 4 for flexographic printing was prepared according to the formula shown in Table 8.

TABLE 8

Flexographic reagent varnish 4

| Material | Weight |
|---|---|
| Methyl cellulose 15 cps | 5.5 gm |
| Glucose oxidase (GOD) | 50,000 U |
| Peroxidase (POD) | 43,5000 U |
| 4-Aminoantipyrin (4-AAP) | 500 mg |
| 2,4,6 Tribromo-3-hydroxyl benzoic acid (TBHBA) | 450 mg |
| L-Cystein | 15 mg |
| Gallic acid | 50 mg |
| Fill up with water to 100 gm | |

The Example 4 varnish was printed on a flexographic press using a flexo plate and anilox roller that provided a pick-up volume of 20 cm³/m² to 30 cm³/m². The substrate was MH2384BL paper. The flexo plate had a set of three bands, printed at different volumes, including full-tone and half-tone areas (100%, 60%, and 30%). After printing, the prints were cut into strips having a width of 0.5 cm to 1.0 cm, and a length of 8 cm to 10 cm, for the glucose test. The color changes for Examples 3 and 4 were similar to those for Examples 1 and 2.

Examples 5 to 8. Additional Reagent Varnish Formulations

Additional reagent varnishes 5 to 8, suitable for flexographic or gravure printing, were prepared. The formulations of Examples 5 to 8 are shown in Tables 9 to 12.

TABLE 9

Reagent varnish 5

| Material | Weight |
|---|---|
| Methyl cellulose 400 cps | 1.3 gm |
| Glucose oxidase (GOD) | 31,000 U |
| Peroxidase (POD) | 7,500 U |
| 4-Aminoantipyrin (4-AAP) | 250 mg |
| 4-Hydroxybenzoic acid (4-HBA) | 420 mg |
| Gallic acid | 50 mg |
| Fill up with water to 100 gm | |

TABLE 10

Reagent varnish 6

| Material | Weight |
|---|---|
| Gelatin | 2.2 gm |
| Glucose oxidase (GOD) | 31,000 U |
| Peroxidase (POD) | 7,500 U |
| 4-Aminoantipyrin (4-AAP) | 250 mg |
| 4-Hydroxybenzoic acid (4-HBA) | 220 mg |
| 4-Bromophenol | 200 mg |
| Fill up with water to 100 gm | |

TABLE 11

Reagent varnish 7

| Material | Weight |
|---|---|
| Polyvinylpyrrolidone | 4.0 gm |
| Glucose oxidase (GOD) | 31,000 U |
| Peroxidase (POD) | 7,500 U |
| Tetramethylbenzidin TMB | 250 mg |
| 4-Hydroxybenzoic acid (4-HBA) | 220 mg |
| 4-Chlorphenol | 200 mg |
| Fill up with water to 100 gm | |

TABLE 12

Reagent varnish 8

| Material | Weight |
|---|---|
| Methyl cellulose 400 cps | 1.3 gm |
| Glucose oxidase (GOD) | 35,000 U |
| Peroxidase (POD) | 45,000 U |
| Tetramethylbenzidin TMB | 400 mg |
| 4-Hydroxybenzoic acid (4-HBA) | 400 mg |
| 4-Bromophenol | 100 mg |
| Fill up with water to 100 gm | |

The reagent varnishes 5 to 8 can be used as described for varnishes 1 to 4.

Example 9. Silk-Screening Reagent Varnish 9

A varnish suitable for screen printing, reagent varnish 9, was prepared. The formulation of reagent varnish 9 is shown in Table 13.

TABLE 13

Reagent varnish 9

| Material | Weight |
|---|---|
| Methyl cellulose 400 cps | 4.0 gm |
| Glucose oxidase (GOD) | 20,000 U |
| Peroxidase (POD) | 15,000 U |
| 4-Aminoantipyrin (4-AAP) | 400 mg |
| 2,4,6 Tribromo-3-hydroxyl benzoic acid (TBHBA) | 400 mg |
| Gallic Acid | 10 mg |
| Fill up with water to 100 gm | |

The present invention has been described in detail, including the preferred embodiments thereof. However, it will be appreciated that those skilled in the art, upon consideration of the present disclosure, may make modifications and/or improvements on this invention that fall within the scope and spirit of the invention.

What is claimed is:

1. A method of preparing an indicator test strip for determining glucose concentration in a liquid sample, comprising:
    a) providing a reagent varnish, wherein the reagent varnish comprises:
        i. one or more binders;
        ii. one or more oxidase enzymes, wherein each oxidase enzyme is independently present in an amount of 10,000 U/dl to 50,000 U/dl;
        iii. one or more peroxidase enzymes, wherein each peroxidase enzyme is independently present in an amount of 10,000 U/dl to 45,000 U/dl;
        iv. one or more chromogens, wherein each chromogen is independently present in an amount of 200 mg/dl to 750 mg/dl, wherein the chromogens are selected from the group consisting of tribromo hydroxyl benzoic acid (TBHBA), 4-aminoantipyrin (4-AAP), antipyrine, hydroxyl benzoic acid, 2,2'-azino-bis(3-ethylbenzothiazoline-6-sulphonic acid) (ABTS), and combinations thereof;
        v. one or more neutralizers; and
        vi. water;
    b) providing a substrate;
    c) printing the reagent varnish onto the substrate; and
    d) drying the reagent varnish on the substrate;
wherein the test strip changes color upon exposure to glucose.

2. The method of claim 1, wherein the binder of the reagent varnish is selected from the group consisting of methylcellulose, hydroxyl ethyl cellulose, ethylcellulose, polyvinylpyrrolidone, polyurethane, gelatin, and combinations thereof.

3. The method of claim 1, wherein the binder is methyl cellulose with a molecular weight of 10,000 to 70,000 Daltons, and a viscosity of 15 to 2,200 cps at 2% solids solution at 20° C.

4. The method of claim 1, wherein at least one of the oxidase enzymes of the reagent varnish is glucose oxidase.

5. The method of claim 1, wherein at least one of the peroxidase enzymes of the reagent varnish is horseradish peroxidase.

6. The method of claim 1, wherein a single chromogen is present in the reagent varnish.

7. The method of claim 1, wherein the one or more neutralizers of the reagent varnish are selected from the group consisting of L-cysteine, mercaptans, thiosulfates, gallic acid, ascorbic acid, and combinations thereof.

8. The method of claim 1, wherein the substrate is cellulosic.

9. The method of claim 8, wherein the cellulosic substrate is a paper with a thickness of equal to or greater than 100 μm, and with a basic weight of equal to or greater than 80 g/m².

10. The method of claim 1, wherein the substrate is coated paper; or wherein the substrate is a plastic film with a thickness of equal to or greater than 40 μm.

11. The method of claim 10, wherein the coated paper substrate is inkjet paper with surface structure; or wherein the coated paper substrate is embossed coated paper with linen surface.

12. The method of claim 1, wherein the reagent varnish is printed on the substrate via flexographic printing, gravure printing, or screen printing.

13. The method of claim 1, wherein the reagent varnish is printed on the substrate with a wet coating weight of 4 to 40 g/m².

14. The method of claim 1, wherein the printing is performed using a gravure cylinder with a cell depth of 30 to 400 μm; or wherein the printing is performed using a flexographic anilox roll with a pick-up volume from 7 to 40 cm³/m²; or wherein the printing is performed using a synthetic mesh screen of 60-150 threads/cm.

15. The method of claim 1, wherein a single band of reagent varnish is printed on the substrate.

16. The method of claim 1, wherein multiple discrete regions of the substrate are printed at different coating weights, to provide varying amounts of reagent varnish in each region.

17. The method of claim 16, wherein the discrete regions provide differing intensities of color change upon exposure to glucose.

18. A test strip prepared by the method of claim 1, suitable to test glucose concentration in a liquid sample.

19. A method of testing glucose concentration in a liquid sample, comprising the steps of:
   a) providing the test strip of claim 18;
   b) contacting the test strip with a liquid sample; and
   c) observing a visual color change, wherein the color intensity indicates the level of glucose.

* * * * *